United States Patent
Matsumoto

(10) Patent No.: US 7,590,506 B2
(45) Date of Patent: Sep. 15, 2009

(54) PATTERN MEASUREMENT APPARATUS AND PATTERN MEASURING METHOD

(75) Inventor: Jun Matsumoto, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 11/728,822

(22) Filed: Mar. 27, 2007

(65) Prior Publication Data
US 2008/0015813 A1 Jan. 17, 2008

(30) Foreign Application Priority Data
Mar. 29, 2006 (JP) ............................. 2006-090290
Feb. 21, 2007 (JP) ............................. 2007-040858

(51) Int. Cl.
*G01B 5/004* (2006.01)

(52) U.S. Cl. ..................................... 702/167

(58) Field of Classification Search ................... 702/39, 702/40, 56, 66, 70, 71, 73, 83, 147, 167, 702/179; 257/48; 378/54; 382/149
See application file for complete search history.

(56) References Cited

U.S. PATENT DOCUMENTS

2002/0000550 A1* 1/2002 Yang et al. ..................... 257/48
2002/0116135 A1* 8/2002 Pasika et al. ................... 702/21
2004/0057551 A1* 3/2004 Skatter et al. .................. 378/54
2004/0146194 A1 7/2004 Ichikawa et al.
2005/0207673 A1 9/2005 Takane et al.
2005/0226494 A1* 10/2005 Yamamoto et al. .......... 382/149

FOREIGN PATENT DOCUMENTS

| JP | 05-296754 | 11/1993 |
|---|---|---|
| JP | 2005-195361 | 7/2005 |
| WO | WO 96/21195 | 7/1996 |

OTHER PUBLICATIONS

Bryan S Morse, Edge Detection, 2000, Brigham Young University, pp. 1-6.*

* cited by examiner

*Primary Examiner*—Edward Raymond
*Assistant Examiner*—Mohamed Charioui
(74) *Attorney, Agent, or Firm*—Muramatsu & Associates

(57) ABSTRACT

A pattern measurement apparatus includes a line profile creating unit for creating a line profile of a pattern formed on a sample by scanning with a charged particle beam, a derivative profile creating unit for creating a second derivative profile by differentiating twice the line profile, and an edge detecting unit for judging whether an edge in the pattern is a rising edge or a falling edge. Assuming that the two peak positions appearing in the vicinity of the edge position of the pattern obtained from the second derivative profile are defined as X1 and X2, X2 being larger than X1, the edge detecting unit judges that the edge is a rising edge when a signal amount in the peak position X1 is larger than a signal amount in the peak position X2.

9 Claims, 9 Drawing Sheets

FIG. 8

| PEAK POSITIONS OBTAINED BY FIRST DERIVATION OF LINE PROFILE | PEAK POSITIONS AND PEAK VALUES OBTAINED BY SECOND DERIVATION OF LINE PROFILE | | JUDGMENT WHETHER EDGE PORTION IN PATTERN IS RISING EDGE OR FALLING EDGE |
|---|---|---|---|
| X1 | X11 | P11 | RISING EDGE |
|  | X12 | P12 |  |
| X2 | X21 | P21 | FALLING EDGE |
|  | X22 | P22 |  |
| X3 | X31 | P31 |  |
|  | X32 | P32 |  |

PATTERN MEASUREMENT APPARATUS AND PATTERN MEASURING METHOD

CROSS-REFERENCE TO RELATED APPLICATIONS

This application is based on and claims priority of Japanese Patent Applications No. 2006-090290 filed on Mar. 29, 2006, and No. 2007-040858 filed on Feb. 21, 2007, the entire contents of which are being incorporated herein by reference.

BACKGROUND OF THE INVENTION

1. Field of the Invention

The present invention relates to a measurement apparatus and a measuring method for a pattern using a charged particle beam. More specifically, the present invention relates to a pattern measurement apparatus and a pattern measuring method capable of distinguishing between lines and spaces provided at even intervals in a spaced line-and-space pattern.

2. Description of the Prior Art

Measurement using a scanning electron microscope has heretofore been applied to a line-width measuring method of a pattern. Here, a scanning electron microscope is configured to scan an electron beam scanning range by irradiating incident electrons, to acquire secondary electrons emitted from a sample by using a scintillator, to convert a quantity of electrons thus acquired into luminance, and to display a surface image of the sample on a display device.

In the case of managing characteristics of a semiconductor device by use of this scanning electron microscope, it is a general practice to check whether or not a line width of a pattern is formed in the size within a design standard. The management of the pattern line width is typically executed in accordance with the following procedures. Specifically, after displaying a predetermined range of a pattern formed on a photomask on a display device, an electron beam is focused and irradiated on a measurement point in the displayed range to acquire a waveform of luminance distribution based on secondary electrons reflected from the measurement point. Then, a high-level width in the waveform of luminance distribution is determined as a line width. A judgment is made as to whether or not this line width falls within an acceptable error range. If the line width is within the acceptable error range, a subsequent process is executed. In contrast, if the line width is out of the acceptable error range, the photomask is sent back to a process for forming the pattern.

In this way, the line-width measurement of the pattern is important in the manufacturing process of the semiconductor device, and various methods for accurately measuring the line width have been disclosed.

A position where a slope of luminance corresponding to a quantity of secondary electrons becomes the maximum is generally defined as an edge position of the pattern, whereas Japanese Patent Application Laid-open Publication No. Hei 5(1993)-296754 discloses an edge detection method of determining, as an edge position, a position where a secondary electron signal becomes the minimum.

Meanwhile, Japanese Patent Application Laid-open Publication No. 2005-195361 discloses a method of calculating an average line width and an average space width from autocorrelation values between an original image obtained by differentiating once luminance information of a line-and-space pattern and a shifted image in the x direction.

As described above, the line-width measurement of the pattern with a scanning electron microscope employs the method of determining the position where the slope of luminance becomes the maximum as the edge position or the method of determining the position where the secondary electron signal becomes the minimum as the edge position.

However, application of these methods of detecting the edge position to the line-and-space pattern turns out to cause the following problem.

When the width of a line pattern is approximately equal to the width of a space pattern, it is possible to detect edges, but it is difficult to judge whether intervals between the edges constitute the line pattern or the space pattern.

In contrast, it is possible to judge whether the intervals constitute the line pattern or the space pattern by considering the luminance (tone) information of the pattern. For example, the tone of a line pattern 63a is usually higher than the tone of a space pattern 62a as shown in FIG. 1A. It is therefore possible to judge that the pattern 63a between edges 61 having the higher tone is the line pattern.

Nevertheless, there are various types of constituent material or ranges of film thickness that may cause a line pattern 63b and a space pattern 62b not to have a difference in the tone as shown in FIG. 1B or a case in which the tone relation between a line pattern 63c and a space pattern 62c is reversed as shown in FIG. 1C. In such cases, there is a risk of misjudging whether a portion between the edges constitutes the line pattern or the space pattern.

There have been no reports concerning techniques for distinguishing between the line pattern and the space pattern in the line-and-space pattern in which the line width and the space width are set almost equal to each other.

SUMMARY OF THE INVENTION

The present invention has been made in view of the above-mentioned problem of the related art. An object of the present invention is to provide a pattern measurement apparatus and a pattern measuring method capable of distinguishing between a line pattern and a space pattern even when tones of lines and spaces are reversed in a measurement target including the lines and spaces formed almost at even intervals.

Moreover, another object of the present invention is to provide a pattern measurement apparatus and a pattern measuring method capable of accurately specifying irregularities in a measurement target region without being influenced by luminance of a pattern.

The above-mentioned problem is solved by providing a pattern measurement apparatus which includes a line profile creating unit for creating a line profile of a pattern formed on a sample by scanning with a charged particle beam, a derivative profile creating unit for creating a second derivative profile by differentiating twice the line profile, and an edge detecting unit for judging whether an edge in the pattern is a rising edge or a falling edge by use of two peak positions and two peak values appearing in the vicinity of an edge position of the pattern obtained from the second derivative profile.

In the pattern measurement apparatus according to this aspect, assuming that the two peak positions appearing in the vicinity of the edge position of the pattern obtained from the second derivative profile are defined as X1 and X2 (X2>X1), the edge detecting unit may be configured to judge that the edge is a rising edge when a signal amount in the peak position X1 is larger than a signal amount in the peak position X2 and that the edge is a falling edge when the signal amount in the peak position X1 is smaller than the signal amount in the peak position X2.

According to the present invention, the second derivative profile is created by differentiating twice the line profile and a judgment is made as to whether the edge in the pattern is the rising edge or the falling edge by use of the two peak positions and the two peak values, and by determining which positions appear in the vicinity of the edge position of the pattern obtained from the second derivative profile. In this judgment, assuming that the two peak positions are defined as X1 and X2, for example, signal intensity in the position X1 is compared with signal intensity in the position X2. Then, the edge position is judged as the rising edge in the direction from the position X1 to the position X2 when the signal intensity in the position X1 is larger than the signal intensity in the position X2. In this way, even in the case of a line-and-space pattern including line patterns and space patterns formed almost at even intervals, it is possible to detect the line pattern reliably.

Meanwhile, the above-mentioned problem is solved by a pattern measuring method which includes the steps of creating a line profile of a pattern formed on a sample by scanning the sample with a charged particle beam, creating a second derivative profile by differentiating twice the line profile, and judging whether an edge in the pattern is a rising edge or a falling edge by use of two peak positions and two peak values, which peak positions appear in the vicinity of an edge position of the pattern obtained from the second derivative profile.

In the present invention, the second derivative profile is created by differentiating twice the line profile and a judgment is made as to whether the edge in the pattern is the rising edge or the falling edge by use of the two peak positions and the two peak values which peak positions appear in the vicinity of the edge position of the pattern obtained from the second derivative profile. In this way, even in the case when a line width and a space width are almost equal, it is possible to identify the line pattern and to measure the width of the line pattern.

BRIEF DESCRIPTION OF THE DRAWINGS

FIG. 8 is an example of a table of correlations between peak positions based on first derivative and second derivative.

DESCRIPTION OF THE PREFERRED EMBODIMENT

Now, an embodiment of the present invention will be described below with reference to the accompanying drawings.

A configuration of a scanning electron microscope used as a pattern measurement apparatus will be described in the first place. Then, a typical method of measuring a line width of a pattern will be described. Thereafter, pattern detection in the case where lines and spaces are formed at almost even intervals will be described. In particular, a pattern detecting method capable of distinguishing between lines and spaces in the case of reversed tones of the lines and the spaces will be described herein. Lastly, a pattern measuring method using the pattern detecting method of the present invention will be described.

(Configuration of a Scanning Electron Microscope)

Figure 1A:
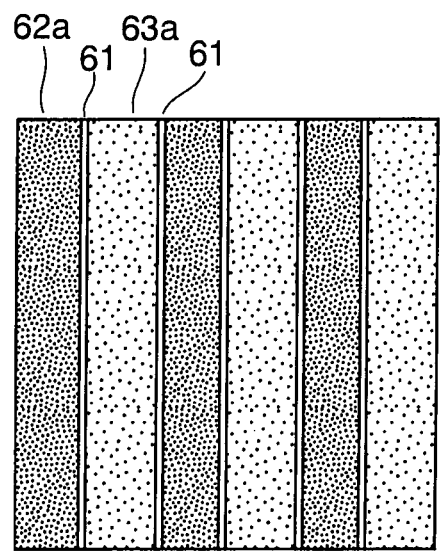
FIGS. 1A to 1C are diagrams showing examples of scanning electron microscopic images of line-and-space patterns.
Figure 1B:
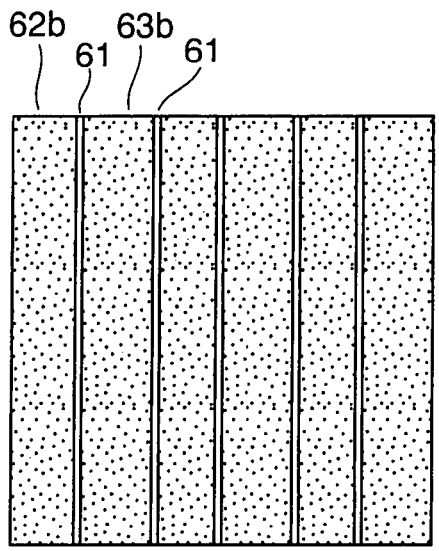
Figure 1C:
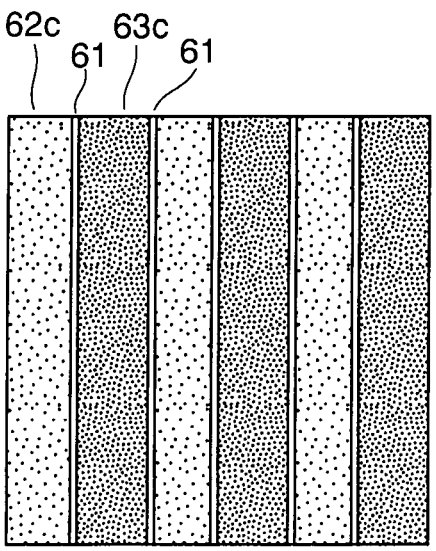
Figure 2:
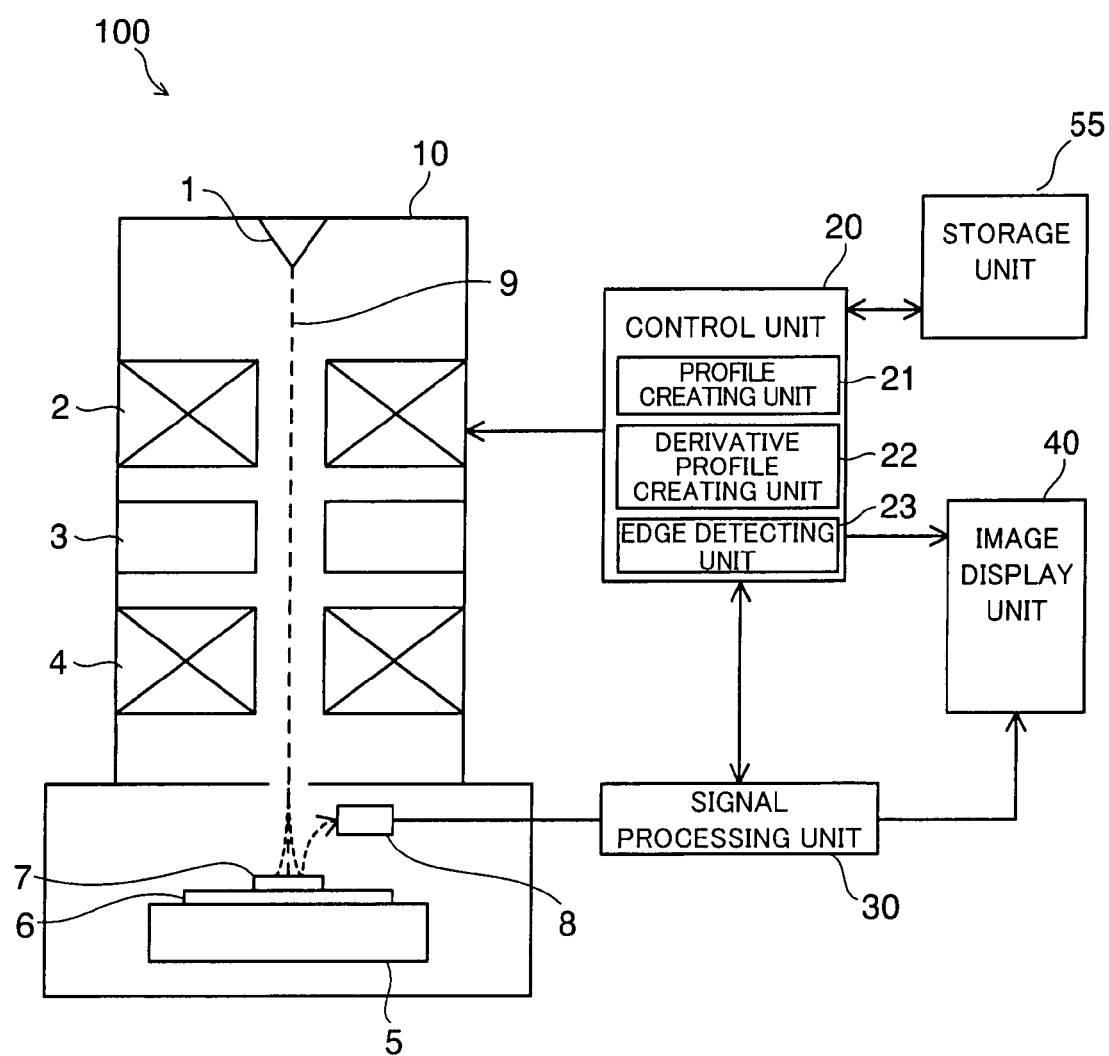
FIG. 2 is a block diagram of a scanning electron microscope used in an embodiment of the present invention.

FIG. 2 is a block diagram of a scanning electron microscope according to an embodiment of the present invention.

This scanning electron microscope 100 essentially includes an electron scanning unit 10, a signal processing unit 30, an image display unit 40, a storage unit 55, and a control unit 20 for controlling the electron scanning unit 10, the signal processing unit 30, the image display unit 40, and the storage unit 55. The control unit 20 includes a profile creating unit 21, a derivative profile creating unit 22, and an edge detecting unit 23.

The electron scanning unit 10 includes an electron gun 1, a condenser lens 2, a deflecting coil 3, an object lens 4, a motion stage 5, and a sample holder 6.

Charged particles 9 are emitted from the electron gun 1 and irradiated onto a sample 7 on the motion stag 5 through the condenser lens 2, the deflecting coil 3, and the object lens 4.

Secondary electrons emitted from the sample 7 upon irradiation of the charged particles 9 are detected by an electron detector 8 formed of a scintillator, for example, and a detected quantity of secondary electrons is converted into a digital amount by an AD converter of the signal processing unit 30 and is then stored in the storage unit 55 as image data. The image data are converted into luminance signal used for display on the image display unit 40. Here, the image data also include information on a range of an acquired image, a magnification of the semiconductor electron microscope (SEM), and so forth. An electron deflection amount by the deflecting coil 3 and an image scanning amount by the image display unit 40 are controlled by the control unit 20. Meanwhile, the control unit 20 stores a program for executing line-width measurement.

The profile creating unit 21 creates a line profile for representing the luminance signal of the SEM image data in a designated range. The line profile represents the luminance signal corresponding to an amount of the secondary electrons, which is deemed to reflect a cross-sectional shape of a measured pattern.

The derivative profile creating unit 22 provides the line profile with a first differentiating process and a second differentiating process to create a first derivative profile and a second derivative profile.

The edge detecting unit 23 detects edges in the pattern out of the line profile, the first derivative profile, and the second derivative profile.

(Typical Method of Measuring Line Width of Pattern)

Next, a typical method of measuring a line width of a pattern on a sample shown in FIG. 3A by use of the scanning electron microscope 100 illustrated in FIG. 2 will be described.

Figure 3A:
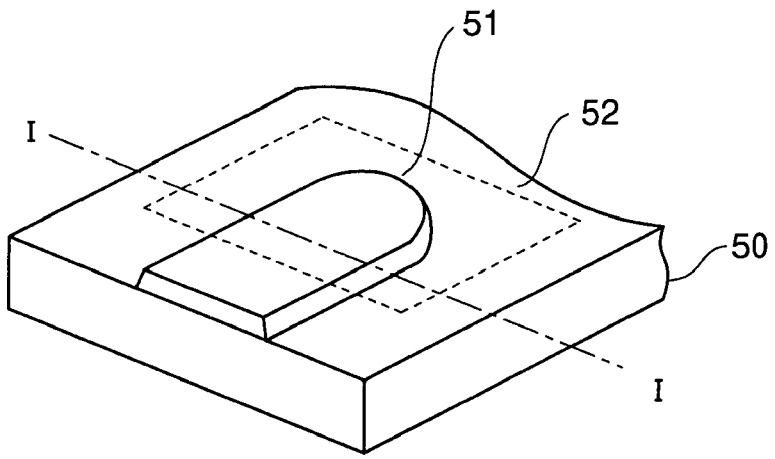
FIGS. 3A to 3C are diagrams for explaining electron images and a profile acquired by a signal processing unit.

As shown in FIG. 3A, the sample 7 used herein includes a foundation layer 50 formed on a semiconductor wafer, and a line pattern 51 formed on the foundation layer 50. Part of the sample 7 is formed into a planar shape as shown in FIG. 3A. Here, a portion surrounded by a broken line 52 indicates an observation area of the scanning electron microscope 100.

Figure 3B:
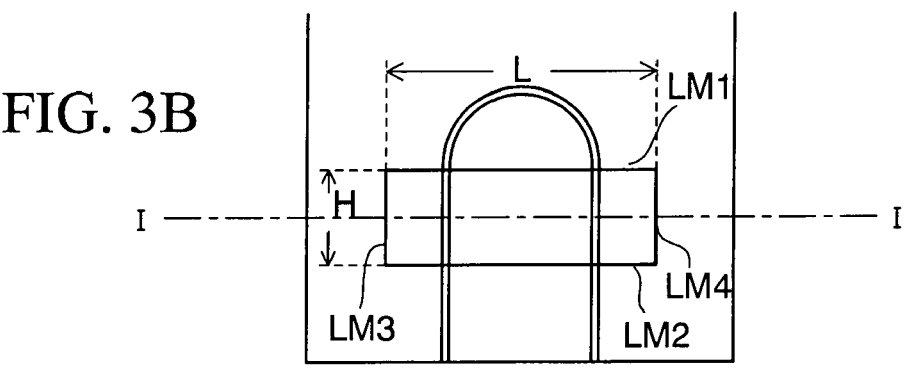

FIG. 3B shows an example of an SEM image, which is achieved by detecting the quantity of electrons such as secondary electrons with the electron detector 8 by scanning the sample shown in FIG. 3A with an electron beam, converting the detected quantity of electrons into the luminance signal, and forming the image display by synchronizing the electron beam scanning and CRT (cathode-ray tube) scanning of the display device.

Another SEM image is extracted from the SEM image shown in FIG. 3B by designating a length measurement area. The length measurement area is defined as L×H=400 pixels, for example. An operator selects this area by defining an upper line marker LM1, a lower line marker LM2, a left line marker LM3, and a right line marker LM4.

The extracted SEM image data are divided in the H direction of the length measurement area, and a line profile corresponding to luminance distribution is obtained for each divided area. When obtaining the line profile, it is possible to reduce noise components by performing a smoothing process at a 3-pixel width in the length L direction, for example.

Figure 3C:
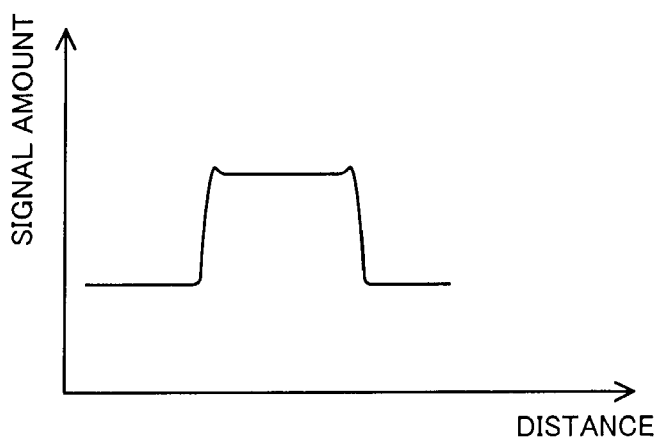

FIG. 3C is a diagram showing the line profile corresponding to the quantity of the secondary electrons emitted from the sample, which is obtained at the time of irradiating the electron beam along the I-I line in FIG. 3A. As shown in FIG. 3C, the line profile steeply changes at an edge portion in the pattern. To find a position of such a steep change, the maximum peak and the minimum peak of derivative signal amounts are found by differentiating the line profile. The width of the line pattern is defined as a distance between a position of this maximum peak and a position of this minimum peak.

This process is performed respectively on the divided areas, and each of average values of the pattern width calculated for the respective regions is defined as a length measurement value.

(Pattern Detection when Lines and Spaces are Formed at Almost Even Intervals)

Figure 4:
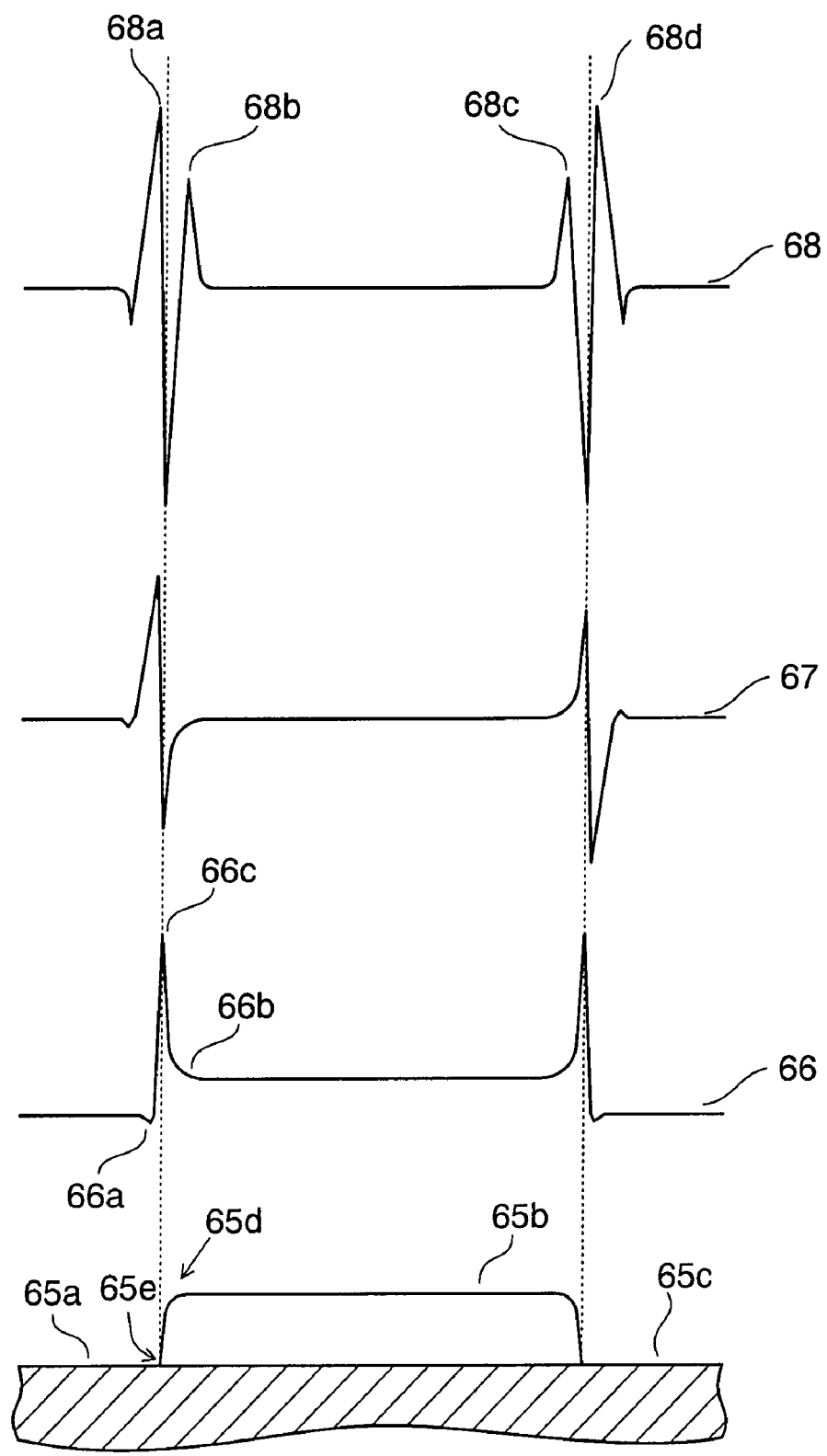
FIG. 4 is a diagram for explaining profiles of a line pattern.
Figure 5:
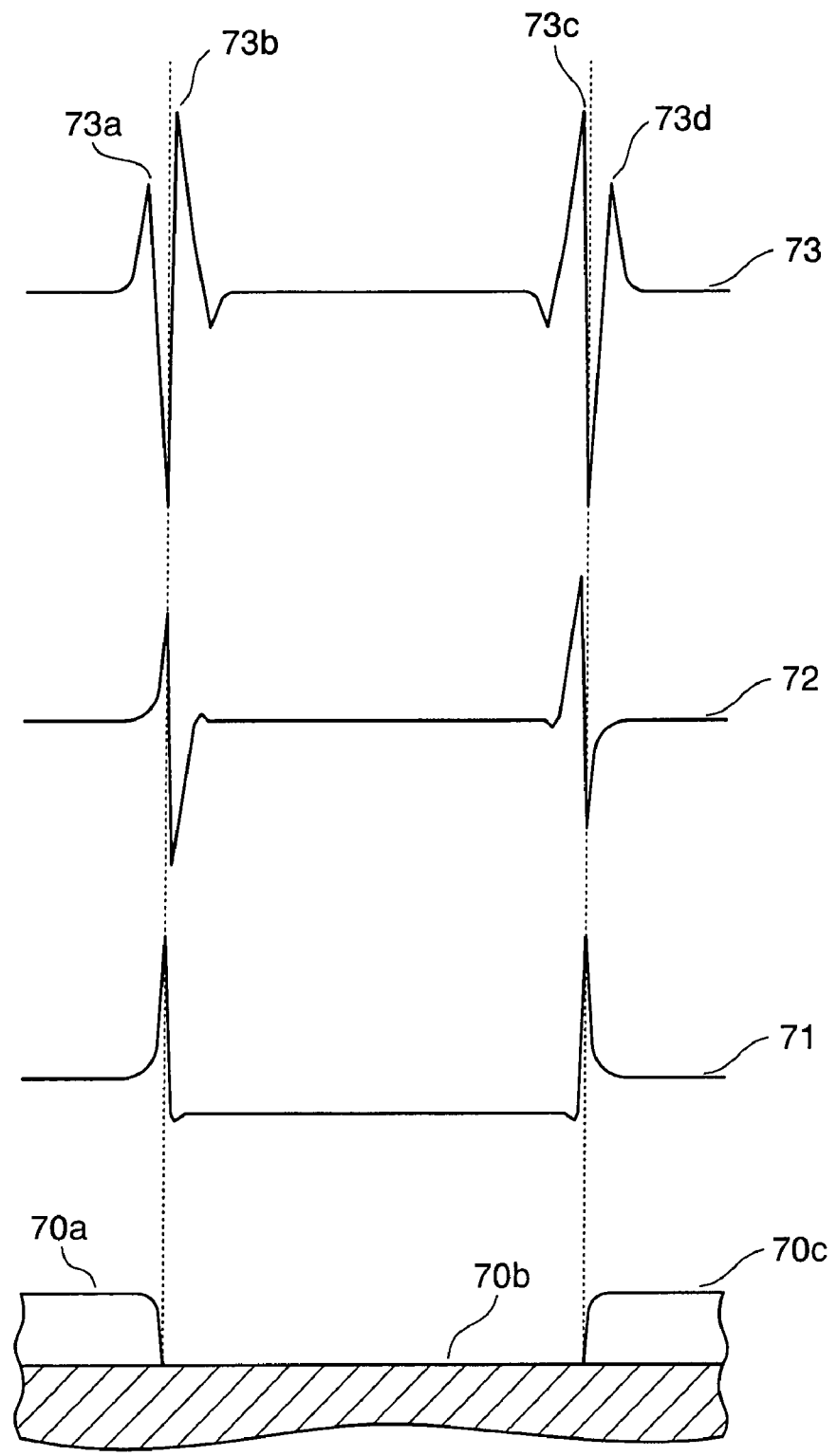
FIG. 5 is a diagram for explaining profiles of a space pattern.

FIG. 4 and FIG. 5 show line profiles representing the luminance signal obtained from SEM images of a line-and-space pattern, first derivative profiles found by differentiating once the line profiles, and second derivative profiles found by differentiating twice the line profiles.

FIG. 4 shows a line profile 66 corresponding to a portion of a line pattern 65b interposed between spaces (portions where no patterns are formed) 65a and 65c, a first derivative profile 67, and a second derivative profile 68.

As shown in the line profile 66 in FIG. 4, a signal amount is increased at a boundary between the space 65a and the line pattern 65b and at a boundary between the line pattern 65b and the space 65c. Moreover, the signal amount at the line pattern 65b is larger than the signal amounts at the space 65a and the space 65c.

In general, a position having the steepest inclination in a line profile is defined as an edge of a pattern. To calculate the steepest position, the line profile is differentiated once to find the maximum value and the minimum value in the first derivative profile.

As it is apparent in the first derivative profile 67 in FIG. 4, the maximum value is found at a position corresponding to the boundary between the space 65a and the line pattern 65b and the minimum value is found at a position corresponding to the boundary between the line pattern 65b and the space. 65c. These positions having the maximum value and the minimum value show the boundaries between the spaces and the pattern, i.e. edge positions. In this way, the edge positions are found by calculating the positions of the maximum value and the minimum value in the first derivative profile 67.

Moreover, as shown in FIG. 4, the boundary between the space 65a and the line pattern 65b, i.e. a rising edge of the line pattern 65b has the maximum value. Meanwhile, the boundary between the line pattern 65b and the space 65c, i.e. a falling edge of the line pattern 65b has the minimum value.

Nevertheless, this relation does not always hold true. To be more precise, the maximum value and the minimum value in the first derivative profile depend on the luminance signal amount of the line profile. Accordingly, there may be a case where the minimum value of the first derivative is located on the rising edge of the pattern, for example. For this reason, in this embodiment, the rising edge and the falling edge of the pattern are identified by use of the second derivative profile.

As shown in the second derivative profile 68 in FIG. 4, two peaks 68a and 68b, each having a different intensity value, appear in the vicinity of the position corresponding to the edge of the line pattern 65b adjacent to the space 65a. The positions (the sequence) of appearance of these two peaks 68a and 68b, each having the different signal amount, turn out to be different depending on whether the edge is the rising edge or the falling edge. On the rising edge of the line pattern 65b adjacent to the space 65a, the peak 68a having a large signal amount appears on the left side in FIG. 4 while the peak 68b having a smaller signal amount than the peak 68a appears on the right side thereof. On the other hand, on the falling edge of the pattern 65c adjacent to the space 65c, a peak 68c having a smaller signal amount out of the two peaks appears on the left side while a peak 68d having a larger signal amount appears on the right side thereof. Consequently, it is possible to judge whether the edge is the rising edge or the falling edge depending on the sequence of the two peak position.

Assuming that the peak value in the peak position X1 out of the two peak positions is defined as P1 while the peak value in the peak position X2 (X2>X1) is defined as P2, it is possible to judge that the edge is the rising edge of the pattern if P1>P2, and that the edge is the falling edge of the pattern if P1<P2.

The reasons for the above-described capability of distinguishing between the rising edge and the falling edge by differentiating twice the line profile calculated based on the SEM image are as follows.

In the line profile 66 shown in FIG. 4, a quantity of secondary electron discharge is larger on the rising edge of the pattern as compared to a flat portion thereof. Accordingly, the signal amount is increased as indicated by the peak 66c in the line profile. A steep falling waveform 66a is formed on the space 65a side of the peak point 66c while a gentle falling waveform 66b is formed on the line pattern 65b side of the point 66c. Such waveforms are attributable to shapes of the pattern. Specifically, a bottom end 65e of the edge of the pattern forms an angle at a joint between a substrate and the pattern whereas a top end 65d of the edge of the pattern is formed into a slightly rounded corner. It is conceivable that the difference in the shape between the ends of the edge result in the appearance of the steep falling edge 66a and the gentle falling edge 66b.

The difference in the shape between the waveforms 66a and 66b conceivably leads to the difference in the signal amount as a result of the second differentiation.

To be more precise, when the steep portion such as the waveform 66a is differentiated twice, the peak value becomes a large value. Meanwhile, when the gentle portion such as the waveform 66b is differentiated twice, the peak value becomes a small value.

Appearance of the two peaks having the different signal amounts is attributed to the shapes of the pattern. Accordingly, it is possible to distinguish between the rising edge and the falling edge in the pattern.

FIG. 5 shows a line profile 71 corresponding to a portion of a space 70b interposed between line patterns 70a and 70c, a first derivative profile 72, and a second derivative profile 73.

As shown in the line profile 71 in FIG. 5, a signal amount is increased at a boundary between the portion where the line pattern 70a is formed and the space 70b. Similarly, the signal amount is also increased at a boundary between the space 70b and the portion where the line pattern 70c is formed. Moreover, the signal amount of the space 70b is smaller than the signal amounts of the patterns 70a and 70c.

As shown in the first derivative profile 72 in FIG. 5, the minimum value of the signal amount is found at the boundary between the line pattern 70a and the space 70b and the maximum value of the signal amount is found at the boundary between the space 70b and the line pattern 70c. In this way, it is possible to determine the edge positions of the patterns 70a and 70c.

As shown in the second derivative profile 73 in FIG. 5, two peaks 73a and 73b having different signal values appear in the vicinity of the position corresponding to the boundary between the line pattern 70a and the space 70b. In this case, the peak 73a and the peak 73b appear from the left to the right in FIG. 5, and the peak 73a has a small peak value while the peak 73b has a large peak value. Consequently, it is possible to detect the edge of the pattern as the falling edge. Meanwhile, two peaks 73c and 73d having different signal values appear in the vicinity of the position corresponding to the boundary between the space 70b and the line pattern 70c. In this case, the peak 73c and the peak 73d appear from the left to the right in FIG. 5, and the peak 73c has a large peak value while the peak 73d has a small peak value. Consequently, it is possible to detect the edge of the pattern as the rising edge.

Next, a capability of specifying the rising edge and the falling edge even in the case of reversed tones will be described.

Figure 6:
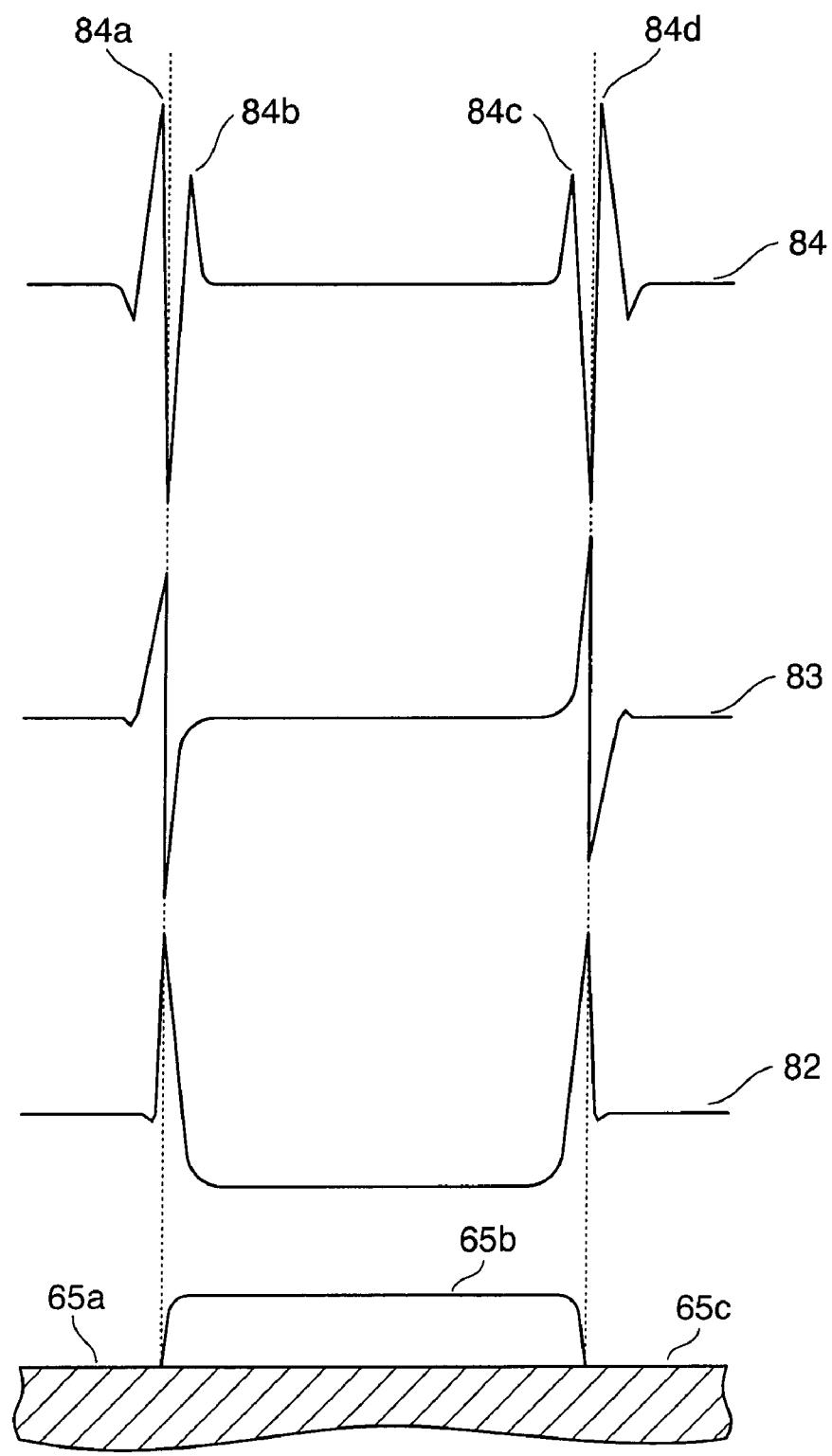
FIG. 6 is a diagram for explaining profiles of the line pattern when luminance is reversed.

FIG. 6 shows various profiles corresponding to the line pattern 65b and the adjacent spaces 65a and 65c, which are the same as FIG. 4. Usually, the luminance of the pattern formed on the substrate exhibits a higher tone than the portions (the spaces) where no patterns are formed. Accordingly, pattern looks white in an image. However, there is a case where the tone relation between the pattern and the space may be reversed owing to the material used for forming the pattern or to the film thickness of the pattern. A line profile 82 in FIG. 6 shows that the signal amount of the line pattern 65b is smaller than the signal amounts of the spaces 65a and 65c. To be more precise, the line profile 82 indicates that the tone of the line pattern 65b is smaller than the tone of the substrate. It is considered that this phenomenon occurs depending on the material of the line pattern 65b or on the film thickness of the line pattern 65b. Here, it is difficult to control such tone variation.

In this case, as shown in a first derivative profile 83 in FIG. 6, the minimum value is located at the boundary between the space 65a and the line pattern 65b and the maximum value is located at the boundary between the line pattern 65b and the space 65c. Since there are the maximum value and the minimum value, it is possible to calculate the positions of the boundaries. However, the boundary between the space 65a and the line pattern 65b has the minimum value in this case. On the other hand, the boundary between the space 65a and the line pattern 65b has the maximum value in FIG. 4. Accordingly, it is not possible to judge whether the edge portion of the pattern is the rising edge or the falling edge merely by use of the maximum value and the minimum value of the first derivative. In other words, if the tones are reversed, the peak values in the edge positions of the first derivative have an inverted relation to the case in FIG. 4. For this reason, it is not possible to judge between the rising edge and the falling edge by use of the peak values.

A second derivative profile 84 in FIG. 6 is obtained by differentiating twice the line profile 82. As shown in this second derivative profile 84, even if the tones are reversed, the relation between the peak values in the two peak positions corresponding to the edge position is the same as the relation shown in FIG. 4. Specifically, two peak values 84a and 84b appear in the vicinity of a position corresponding to the boundary between the space 65a and the line pattern 65b, and the peak values are decreased in the direction from the space 65a to the line pattern 65b. Consequently, this edge is judged as the rising edge. Similarly, two peak values 84c and 84d also appear in the vicinity of a position corresponding to the boundary between the line pattern 65b and the space 65c, and the peak values are increased in the direction from line pattern 65b to the space 65c. Consequently, this edge is judged as the falling edge. In this way, it is possible to judge the rising edge and the falling edge correctly by use of the two peak positions and the two peak values appearing in the vicinity of the edge position in the second derivative profile without an adverse effect of the reversed tones. Accordingly, it is possible to identify the line pattern reliably and thereby to improve measurement throughput of the line pattern width.

(Pattern Measuring Method)

Figure 9:
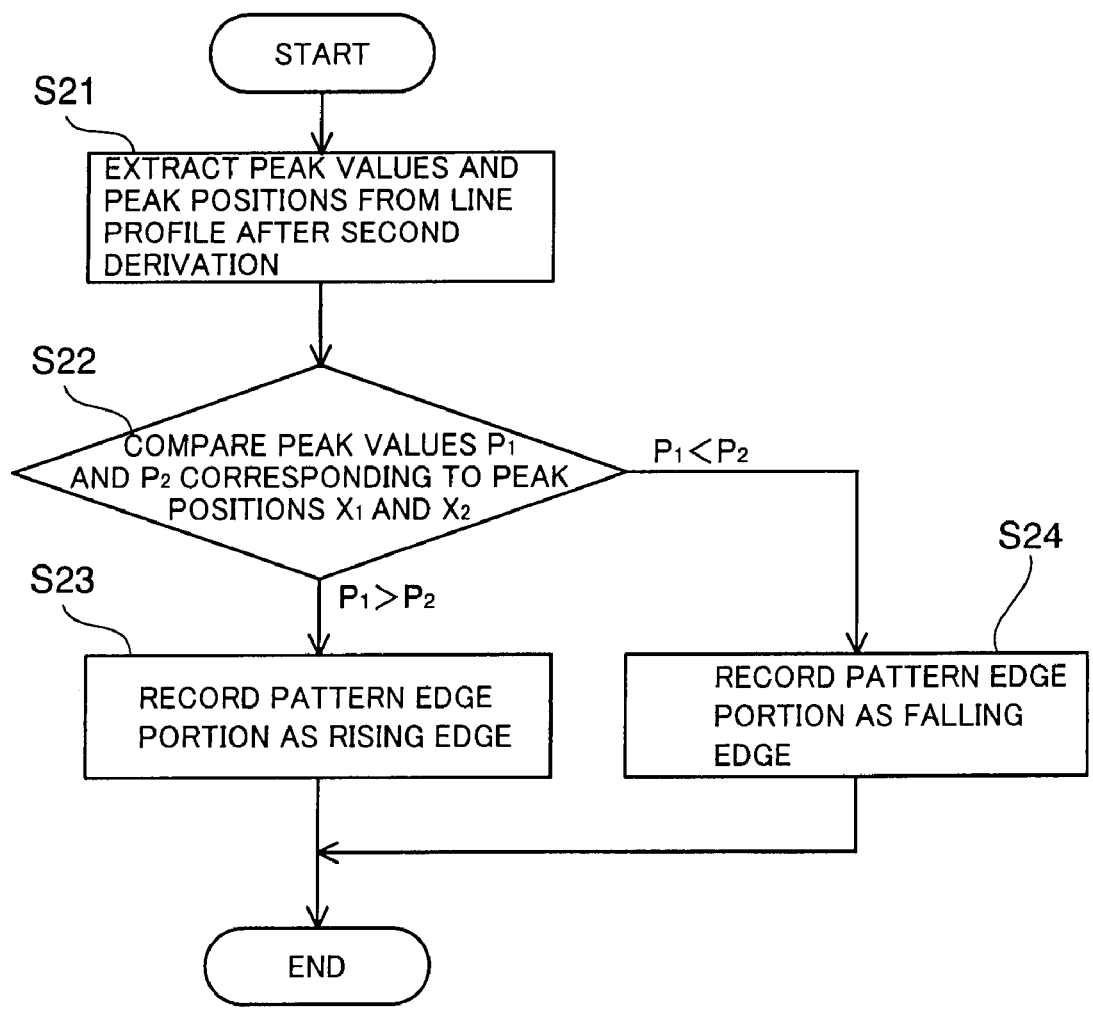
FIG. 9 is a flowchart showing an example of judgment between a rising edge and a falling edge.

Next, a pattern measuring method using an electron beam will be described with reference to FIG. 7, FIG. 8, and FIG. 9.

Figure 7:
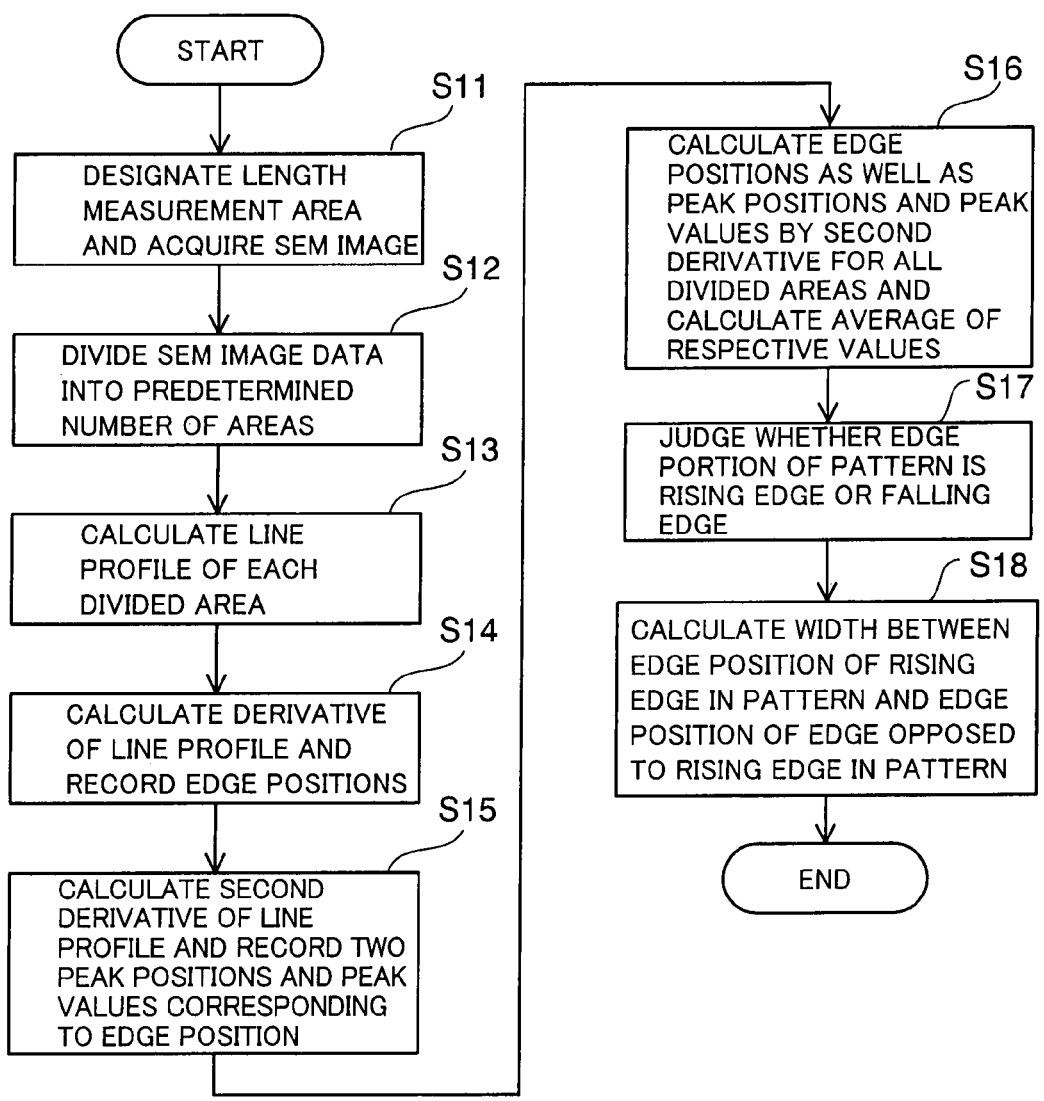
FIG. 7 is a flowchart showing an example of a process to measure a pattern.

FIG. 7 is a flowchart showing an example of a process to measure a line width by identifying a line pattern even when line patterns and space patterns are formed almost at even intervals.

The line-width measurement process shown in FIG. 7 is based on the assumption that a SEM image of a sample formed with a pattern has been acquired in advance and the SEM image data has been stored in the storage unit 55.

First of all, in step S11, a desired length measurement area is designated to acquire a SEM image. Such SEM image data are extracted from the storage unit 55.

Next, in step S12, the SEM image data acquired in step S11 are divided into a predetermined number of areas.

Next, in step S13, a line profile is calculated for each divided area in step S12. Calculation of the line profile is executed by extracting the luminance information out of the SEM image data by use of the profile creating unit 21 of the control unit 20.

Next, in step S14, the line profile calculated in step S13 is differentiated once. The first-differentiation process is conducted by the derivative profile creating unit 22, which employs a differentiation filter such as a Sobel filter used in general image processing. After the first differentiation, the positions having the maximum value and the minimum value of the signal amounts are recorded as the edge positions. For example, the peak positions obtained by the first differentiation are recorded as the edge positions (such as X1) in accordance with a table format as shown in FIG. 8 and are stored in the storage unit 55.

Next, in step S15, the line profile calculated in step S13 is differentiated twice. The second differentiation process is conducted by the derivative profile creating unit 22. As a result of the second differentiation, the two peak positions appearing in the vicinity of each of the edge positions and the peak values in these peak positions are recorded. These values are correlated with the edge positions calculated in step S14 and are stored in the storage unit 55 in the table format. In FIG. 8, the peak positions obtained by the second differentiation corresponding to the edge position X1 are defined as X11 and X12. Upon recording, the peak value in the peak position X11 is defined as P11 and the peak value in the peak position X12 is defined as P12.

Next, in step S16, the peak positions, the peak positions obtained by the second differentiation and the peak values in the peak positions are calculated for all the divided areas in the length measurement area. Specifically, the processes from step S13 to step S15 are executed repeatedly until completing calculation of these values in all the divided areas. Thereafter, averages of the edge positions, the peak positions, corresponding to the edge positions and obtained by the second differentiation, as well as the peak values are calculated and defined as the values of the edge position and so forth in the designated area.

In the next step S17, a judgment is made as to whether the edge portion of the pattern is the rising edge or the falling edge.

In the next step S18, a width of the line pattern is calculated by finding a width between the edge positions of the rising edge in the pattern and the falling edge opposed to rising edge in the pattern, which are judged in the step S17.

Here, a judging process performed in the step S17 as to whether the edge portion of the pattern is the rising edge or the falling edge will be described using a flowchart in FIG. 9.

In the step S21, firstly, the peak position and the peak value in the line profile differentiated twice are extracted from the storage unit 55.

In the next step S22, the size of the peak value P1 in the extracted peak position X1 is compared with the size of the peak value P2 in the peak position X2 (X2>X1). The process goes to step S23 when the peak value P1 is larger than the peak value P2. The process goes to step S24 when the peak value P1 is smaller than the peak value P2.

The next step S23 is executed when the peak value P1 is larger than the peak value P2. Here, the information stating that the edge portion is the rising edge is recorded on the table.

Meanwhile, step S24 is executed when the peak value P1 is smaller than the peak value P2. Here, the information stating that the edge portion is the falling edge is recorded on the table.

As described above, in line-width measurement of a line-and-space pattern, a line profile representing a luminance signal to express strength of a SEM image signal is obtained and a second derivative profile is created by differentiating twice the obtained line profile. Then, based on two peak positions appearing in the vicinity of an edge position in a pattern obtained from the second derivative profile, a judgment is made as to whether the edge of the pattern is a rising edge or a falling edge. This judgment is based on the assumption that the two peak positions are defined as X1 and X2 (X2>X1). Here, a signal amount in the peak position X1 is compared with a signal amount in the peak position X2, and the edge is judged to be the rising edge when the signal amount in the peak position X1 is larger than the signal amount in the peak position X2. In this way, in the line-and-space pattern including line patterns and space patterns formed at almost even intervals, it is possible to detect the line pattern accurately and to measure the line width of the line pattern even in the case of reversed tones between the line pattern and the space pattern.

Moreover, according to this embodiment, the judgment between the rising edge and the falling edge in the pattern is achieved by use of the magnitude of the two peak values in the vicinity of the edge position of the pattern obtained from the second derivative profile. In this way, it is possible to identify an irregular shape accurately even if the pattern is formed into an unknown shape such as a convex shape formed stepwise, a concave shape formed stepwise or a complicated irregular shape. The irregular shape may be displayed according to the information on the identified irregularity.

Furthermore, according to this embodiment, it is possible to distinguish between a rising edge and a falling edge. Accordingly, it is possible to achieve complete automation of the pattern measurement.

Although this embodiment describes the case of using the electron beam as a charged particle beam to be irradiated on the sample, it is to be understood that the present invention is not limited to only this configuration and that the present invention is also applicable to an apparatus using an ion beam, for example.

What is claimed is:

1. A pattern measurement apparatus comprising:
a line profile creating unit for creating a line profile of a pattern formed on a sample by scanning with a charged particle beam;
a derivative profile creating unit for creating a second derivative profile by differentiating twice the line profile; and
an edge detecting unit for judging whether a cross-sectional edge in the pattern is a rising edge or a falling edge based on a relationship between two positive peak positions and two peak values appearing at locations of both sides of each cross-sectional edge of the pattern obtained from the second derivative profile.

2. The pattern measurement apparatus according to claim 1,
wherein, assuming that the two peak positions appearing at the locations of the both sides of each cross-sectional edge of the pattern obtained from the second derivative profile are defined as X1 and X2, X2 being larger than X1, the edge detecting unit judges that the cross-sectional edge is a rising edge when a signal amount in the peak position X1 is larger than a signal amount in the peak position X2.

3. The pattern measurement apparatus according to claim 1,
wherein, assuming that the two peak positions appearing at the locations of the both sides of cross-sectional edge of the pattern obtained from the second derivative profile are defined as X1 and X2, X2 being larger than X1, the edge detecting unit judges that the cross-sectional edge is a falling edge when the signal amount in the peak position X1 is smaller than the signal amount in the peak position X2.

4. The pattern measurement apparatus according to claim 1,
wherein the pattern formed on the sample is a line-and-space pattern in which line patterns are formed at even intervals.

5. A pattern measuring method comprising the steps of:
creating a line profile of a pattern formed on a sample by scanning the sample with a charged particle beam;
creating a second derivative profile by differentiating twice the line profile; and
judging whether a cross-sectional edge in the pattern is a rising edge or a falling edge based on a relationship between two positive peak positions and two peak values appearing at locations of both sides of each cross-sectional edge of the pattern obtained from the second derivative profile.

6. The pattern measuring method according to claim 5,
wherein, assuming that the two peak positions appearing at the locations of the both sides of each cross-sectional edge of the pattern obtained from the second derivative profile are defined as X1 and X2, X2 being larger than X1, the cross-sectional edge is judged to be a rising edge in the step of judging whether the edge in the pattern is a rising edge or a falling edge when a signal amount in the peak position X1 is larger than a signal amount in the peak position X2.

7. The pattern measuring method according to claim 5, wherein, assuming that the two peak positions appearing at the locations of the both sides of the location of the cross-sectional edge of the pattern obtained from the second derivative profile are defined as X1 and X2, X2 being larger than X1, the cross-sectional edge is judged to be a falling edge in the step of judging whether the edge in the pattern is a rising edge or a falling edge when a signal amount in the peak position X1 is smaller than the signal amount in the peak position X2.

8. The pattern measuring method according to claim 5, wherein the pattern formed on the sample is a line-and-space pattern in which line patterns are formed at even intervals.

9. A pattern measurement apparatus, comprising:
means for acquiring a line profile of a pattern formed on a sample by scanning with a charged particle beam,
wherein, according to the magnitudes of values of two peaks in the vicinity of a position of a cross-sectional edge of pattern, which two positive peaks appear at locations of both sides of each cross-sectional edge of the pattern in a second derivative profile obtained by differentiating twice the line profile, a judgment is made as to whether the cross-sectional edge of pattern shown by locations and values of the two positive peaks represents a rising edge or a falling edge.

* * * * *